United States Patent [19]

Jung et al.

[11] Patent Number: 5,608,097
[45] Date of Patent: Mar. 4, 1997

[54] PROCESS FOR PREPARATION OF SILANE COMPOUNDS OF WHICH CHLORINE ATOMS OF C-Cl BONDS HAVE BEEN REDUCED

[75] Inventors: Il N. Jung; Eun J. Cho; Joon S. Han; Yon S. Cho, all of Seoul, Rep. of Korea

[73] Assignee: Korea Institute of Science and Technology, Seoul, Rep. of Korea

[21] Appl. No.: 640,503

[22] Filed: May 1, 1996

[30] Foreign Application Priority Data

Oct. 30, 1995 [KR] Rep. of Korea ................ 38120/1995

[51] Int. Cl.$^6$ ........................................ C07F 7/08
[52] U.S. Cl. ........................................ 556/466
[58] Field of Search ........................................ 556/466

[56] References Cited

U.S. PATENT DOCUMENTS

| | | | |
|---|---|---|---|
| 4,510,136 | 4/1985 | Moberg | 514/63 |
| 4,956,486 | 9/1990 | Marko et al. | 556/466 |
| 5,336,799 | 8/1994 | Kalchauer et al. | 556/466 |

OTHER PUBLICATIONS

F. C. Whitmore, et al., "Hydrogen–Halogen Exchange Reactions of Triethylsilane. A New Rearrangement of Neopentyl Chloride", J. Am. Chem. Soc., vol. 69, (pp. 2108–2110), 1947.

Yu. I. Khudobin, et al., "Dehydrocondensation of Trialkyl-or Arylsilanes with Organic Compounds Containing Hydroxyl Group", Chem. Abstr., vol. 56, (p. 8737), 1962.

R. H. Krieble, et al., "The Preparation and Properties of Some Chloromethylchlorosilanes", J. Am. Chem. Soc., vol. 67, (pp. 1810–1812), 1945.

Joel D. Citron, et al., "Palladium–Catalyzed Reactions of Triorganosilicon Hydrides with Halocarbons", The Journal of Organic Chemistry, vol. 34, (pp. 638–640), 1969.

Primary Examiner—Paul F. Shayer
Attorney, Agent, or Firm—Oblon, Spivak, McClelland, Maier & Neustadt, P.C.

[57] ABSTRACT

The present invention relates to a process for preparation of silane compound represented by general formula (I) of which one or two hydrogens have been substituted, comprising a reaction of silane compound represented by general formula (II) with trichlorosilane in the presence of metal or metal compound as a catalyst.

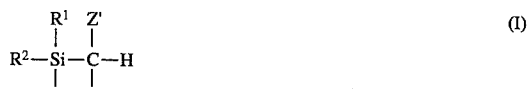

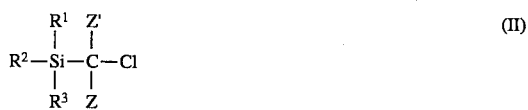

whereby, $R^1$, $R^2$ and $R^3$ respectively represent chlorine or methyl group, and Z and Z' respectively represent hydrogen or chlorine, and as a result, the process of the present invention is industrially useful because trichlorosilane having relatively low price is employed.

6 Claims, No Drawings

PROCESS FOR PREPARATION OF SILANE COMPOUNDS OF WHICH CHLORINE ATOMS OF C-Cl BONDS HAVE BEEN REDUCED

BACKGROUND OF THE INVENTION

1. Field of the Invention

The present invention relates to a process for preparation of silane compounds represented by the following formula (I) of which chlorine atoms of C—Cl bonds have been reduced. More specifically, the present invention relates to a process for preparation of silane compounds of formula (I) of which one or more hydrogens are substituted, wherein a silane compound represented by the following formula (II) is reacted with trichlorosilane in the presence of metal or metal compound catalysts.

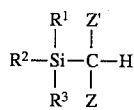

(I)

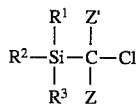

(II)

In the formulas above, $R^1$, $R^2$ and $R^3$ independently represent chlorine or methyl group, and Z and Z' independently represent hydrogen or chlorine.

2. Description of the Prior Art

In 1947, Sommer et al. firstly reported that when triethylsilane compound is reacted with chloroalkane in the presence of aluminum chloride catalyst, a hydrogen of triethylsilane is substituted with a chlorine of the chlorocarbon compound. [F. C. Whitmore, E. W. Pietrusza and L. H. Sommer, J. Am. Chem. Soc., 69, 2108–2110(1947)]

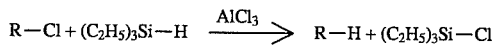

In the above formula, R represents hexyl, neopentyl or neopentylcarbinyl.

In 1958, Khudobin et al. reported that when triethylsilane is reacted with halobenzene in the presence of a metal catalyst such as nickel, cobalt, palladium or platinum, a displacement reaction of hydrogen with halogen occurs. [Yu. I. Khudobin, B. N. Dolgov and P. Kharitonov, Chem. Abstr., 56, 8737(1962)].

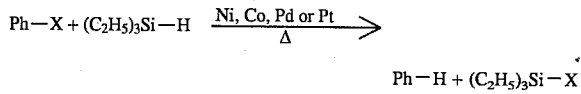

In 1968, Sommer et al. reported that palladium metal adsorbed on active carbon can be used as a catalyst for the same reaction. [J. D. Citron, J. E. Lyons and L. H. Sommer, J. Org. Chem., 34, 638(1969)]

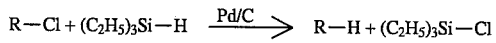

In currently known processes, an organic group of an organic chlorine compound was a simple aliphatic group such as hexyl, neopentyl or neopentylcarbinyl, or an aromatic group, phenyl. However, a reduction reaction of a chlorocarbon having a chlorosilyl group, as an organo-silicon compound has not yet been reported. Further, triethylsilane used as a hydrogen donor is expensive, because it is not industrially manufactured in large scale, whereby the above reaction is not industrially applicable.

SUMMARY OF THE INVENTION

The present inventors discovered the fact that instead of a chlorosilyl group in an organosilicon compound, only bonds between carbon and chlorine of the organosilicon compound, having bonds between silicon and chlorine which can be easily reduced by a reducing agent such as lithium aluminum hydride, can be stepwisely reduced by using trichlorosilane as a hydrogen donor, and thereby achieved the present invention. In particular, trichlorosilane used in the present invention is inexpensive, because it is industrially manufactured. Thus, the process according to the present invention is very economic and industrially usable.

An object of the present invention is to provide a process for preparation of silane compound represented by general formula (I) of which one or two hydrogens are substituted, whereby silane compounds represented by general formula (II) are reacted with trichlorosilane in the presence of metal or metal compound as a catalyst.

DETAILED DESCRIPTION OF THE INVENTION

Catalysts used in the process according to the present invention may be homogeneous catalysts as well as heterogeneous catalysts. In particular, the catalysts are metals or metal compounds used as a catalyst for hydrogen silylation reaction, such as bis(triphenylphosphine)dichloronickel, palladium diacetate, dichloropalladium, chloroplatinic acid, platinum adsorbed on alumina, and platinum adsorbed on active carbon. The amount of catalyst is 0.01 to 20% by mole relative to the compound represented by general formula (II). Catalytic effect can be suffiently obtained by using an amount of 0.01% or more of the catalyst.

In the process according to the present invention, the amount of trichlorosilane is twice or more, preferably 2 to 40 folds, relative to the amount of the compound of general formula (II). The reaction effectively occurs when the amount of trichlorosilane is twice or more.

The reaction occurs in such conditions that the reacting materials are heated at a reaction temperature of 50° to 200° C. for several minutes to several hours. At a temperature which is lower than such range, the reaction rate is too slow; and at a higher temperature, decomposition of compounds may occur.

In the process of the present invention, silane compounds(I) of which two or more chlorines bonded to carbon have been substituted with hydrogen can be obtained by simply increasing the amount of catalyst and the reaction time. For example, if the amount of catalyst and the reaction time are increased twice in the process for preparation of compound (I) of which one hydrogen has been substituted, compound (I) of which two hydrogens have been substituted can be obtained.

The process of the present invention is a reaction process for substituting a chlorine atom bonded to a carbon atom of the compound of formula (II) with hydrogen, and the process is described in more detail hereafter.

In a sealed stainless steel tube, 0.01 to 20% by mole of catalyst and twice or more of trichlorosilane, relative to the compound of general formula (II), are placed together with the compound(II), and then heated at a temperature of 50° to 200° C. for several minutes to several hours. After completing the reaction, the product is subjected to fractional distillation. In order to substitute two or more chlorine atoms bonded to a carbon atom, the amount of catalyst and the reaction time are properly increased from the aforementioned reaction condition.

(Chloromethyl)methyldichlorosilane corresponding to the compound of formula (I) is used as a starting material of an organosilicon sterilizer (fluosilazole) [U.S. Pat. No. 4,510, 136]. This starting material is prepared by chlorination of dimethyldichlorosilane, but in the process by-products such as (polychloromethyl)chlorosilane are obtained in large amount as well as the desired product, (chloromethyl)methyldichlorosilane [R. H. Krieble and J. R. Elliott, J. Am. Chem. Soc., 67, 1810(1945)]. The boiling points of the products obtained from this reaction have little differences, so that it is difficult to separate them. If the (multichloromethyl)chlorosilane compounds are hydrogenated to (chloromethyl)methyldichlorosilane according to the present invention, the by-products can be reused without applying any separating procedures.

According to the present invention, chlorine of C—Cl bond of (multi-chloromethyl)chlorosilane compound obtained as a by-product of chlorination of methyl chlorosilane is substituted with hydrogen by using trichlorosilane having low price, whereby the recycling of by-product is successfully achieved.

DESCRIPTION OF THE PREFERRED EMBODIMENT

Hereinafter, the present invention is described in more detail referring to the examples. However, it is not intended to limit the scope of the present invention to these examples.

EXAMPLE 1

Reduction of (Trichloromethyl)trichlorosilane Using Bis(triphenylphosphine)dichloronickel i) In a sealed stainless tube, 0.10 g of bis(triphenylphosphine)dichloronickel catalyst is placed, and 7.58 g(15 mmol) of (trichloromethyl)trichlorosilane (dissolved in a toluene solvent in 50% by weight concentration) and 10.16 g(75 mmol) of trichlorosilane were introduced thereto. After reacting at 150° C. for 15 minutes, the progress of reaction and identification of the product were performed by an analysis using gas chromatography equipped with a mass analyzer. By a fractional distillation, 2.58 g of (dichloromethyl)trichlorosilane of which a chlorine bonded to a carbon of (trichloromethyl)trichlorosilane compound has been substituted with a hydrogen is obtained as a product [yield: 79%, b.p.:144°–146° C.].

$^1$H NMR (ppm, CDCl$_3$) δ 5.51(s,CH)

ii) According to the same procedure as in Example 1 i), 1.79 g of (chloromethyl)trichlorosilane of which two chlorine atoms of (trichloromethyl)trichlorosilane have been substituted with hydrogen is obtained by reacting the latter at 150° C. for 30 minutes by using 0.20 g of bis(trimethylphosphine)dichloronickel catalyst [yield: 65%, b.p.: 117°–118° C.].

$^1$H NMR (ppm, CDCl$_3$) δ 3.28(s,CH$_2$)

EXAMPLE 2

Reduction of (Trichloromethyl)trichlorosilane Using Palladium Diacetate i) According to the same procedure as Example 1 i), 2.35 g of (dichloromethyl)trichlorosilane of which one chlorine atom of (trichloromethyl)trichlorosilane has been substituted with hydrogen is obtained by reacting the latter at 150° C. for 30 minutes by using 0.03 g of palladium diacetate catalyst [yield: 72%].

ii) According to the same procedure as in Example 1 i), 1.74 g of (chloromethyl)trichlorosilane of which two chlorine atoms of (trichloromethyl)trichlorosilane have been substituted with hydrogen is obtained by reacting the latter at 150° C. for 1 hour by using 0.06 g of palladium diacetate catalyst [yield: 63%].

EXAMPLE 3

Reduction of (Trichloromethyl)trichlorosilane Using Dichloropalladium i) According to the same procedure as in Example 1 i), 2.19 g of (dichloromethyl)trichlorosilane of which one chlorine atom of (trichloromethyl)trichlorosilane has been substituted with hydrogen, is obtained by reacting the latter at 150° C. for 5 hours by using 0.03 g of dichloropalladium catalyst [yield: 67%].

ii) According to the same procedure as in Example 1 i), 1.66 g of (chloromethyl)trichlorosilane of which two chlorine atoms of (trichloromethyl)trichlorosilane have been substituted with hydrogen is obtained by reacting the latter at 150° C. for 9 hours by using 0.06 g of dichloropalladium diacetate catalyst [yield: 60%].

EXAMPLE 4

Reduction of (Trichloromethyl)trichlorosilane Using Chloroplatinic Acid i) According to the same procedure as in Example 1 i), 2.33 g of (dichloromethyl)trichlorosilane of which one chlorine atom of (trichloromethyl)trichlorosilane has been substituted with hydrogen is obtained by reacting the latter at 150° C. for 12 hours by using 150 μl of chloroplatinic acid (0.1M in isopropyl alcohol) catalyst [yield: 72%].

ii) According to the same procedure as in Example 1 i), 1.85 g of (chloromethyl)trichlorosilane of which two chlorine atoms of (trichloromethyl)trichlorosilane have been substituted with hydrogen is obtained by reacting the latter at 150° C. for 24 hours by using 300 μl of chloroplatinic acid (0.1M in isopropyl alcohol) catalyst [yield: 67%].

EXAMPLE 5

Reduction of (Trichloromethyl)trichlorosilane Using Platinum Adsorbed on Alumina i) According to the same procedure as in Example 1 i), 2.10 g of (dichloromethyl)trichlorosilane of which one chlorine atom of (trichloromethyl)trichlorosilane has been substituted with hydrogen is obtained by reacting the latter at 150° C. for 9 hours by using 0.29 g of platinum(1%) adsorbed on alumina as a catalyst [yield: 64%].

ii) According to the same procedure as in Example 1 i), 1.88 g of (chloromethyl)trichlorosilane of which two chlorine atoms of (trichloromethyl)trichlorosilane have been substituted with hydrogen is obtained by reacting the latter at 150° C. for 18 hours by using 0.58 g of platinum(1%) adsorbed on alumina as a catalyst [yield: 68%].

EXAMPLE 6

Reduction of (Trichloromethyl)trichlorosilane Using Platinum Adsorbed on Active Charcoal i) According to the same procedure as in Example 1 i), 2.19 g of (dichloromethyl)trichlorosilane of which one chlorine atom of (trichloromethyl)trichlorosilane has been substituted with hydrogen is obtained by reacting the latter at 150° C. for 24 hours by using 0.29 g of platinum(1%) adsorbed on active charcoal as a catalyst [yield: 67%].

ii) According to the same procedure as in Example 1 ii), 1.79 g of (chloromethyl)trichlorosilane of which two chlorine atoms of (trichloromethyl)trichlorosilane have been substituted with hydrogen is obtained by reacting the latter at 150° C. for 40 hours by using 0.58 g of platinum(1%) adsorbed on active charcoal as a catalyst [yield: 65%].

EXAMPLE 7

Reduction of (Trichloromethyl)methyldichlorosilane Using Bis(triphenylphosphine)dichloronickel i) According to the same procedure as in Example 1 i), 2.35 g of (dichloromethyl)methyldichlorosilane of which one chlorine atom of (trichloromethyl)methyldichlorosilane has been substituted with hydrogen is obtained by reacting 3.49 g (15 mmol) of (trichloromethyl)methyldichlorosilane at 150° C. for 30 minutes [yield: 79%, b.p.:148°–149° C.].

$^1$H NMR (ppm, CDCl$_3$) δ 1.01(s,3H,SiCH$_3$), 5.42(s,1H, CH$_1$)

ii) According to the same procedure as in Example 1 ii), 1.71 g of (chloromethyl)methyldichlorosilane of which two chlorine atoms of (trichloromethyl)methyldichlorosilane have been substituted with hydrogen, is obtained by reacting 3.49 g(15 mmol) of (trichloromethyl)methyldichlorosilane at 150° C. for 1 hour [yield: 70%, b.p.: 121°–122° C.].

$^1$H NMR (ppm, CDCl$_3$) δ 0.92(s,3H,SiCH$_3$), 3.12(s,2H, CH$_2$)

EXAMPLE 8

Reduction of (Trichloromethyl)methyldichlorosilane Using Palladium Diacetate i) According to the same procedure as in Example 2 i), 2.35 g of (dichloromethyl)methyldichlorosilane of which one chlorine atom of (trichloromethyl)methyldichlorosilane has been substituted with hydrogen is obtained by reacting 3.49 g(15 mmol) of (trichloromethyl)methyldichlorosilane at 150° C. for 45 minutes [yield: 79%].

ii) According to the same procedure as in Example 2 ii), 1.76 g of (chloromethyl)methyldichlorosilane of which two chlorine atoms of (trichloromethyl)methyldichlorosilane have been substituted with hydrogen, is obtained by reacting 3.49 g(15 mmol) of (trichloromethyl)methyldichlorosilane at 150° C. for 1 and a half hours [yield: 72%].

EXAMPLE 9

Reduction of (Trichloromethyl)methyldichlorosilane Using Dichloropalladium i) According to the same procedure as in Example 3 i), 2.37 g of (dichloromethyl)methyldichlorosilane of which one chlorine atom of (trichloromethyl)methyldichlorosilane has been substituted with hydrogen, is obtained by reacting 3.49 g(15 mmol) of (trichloromethyl)methyldichlorosilane at 150° C. for 6 hours [yield: 80%].

ii) According to the same procedure as in Example 3 ii), 1.54 g of (chloromethyl)methyldichlorosilane of which two chlorine atoms of (trichloromethyl)methyldichlorosilane have been substituted with hydrogen, is obtained by reacting 3.49 g(15 mmol) of (trichloromethyl)methyldichlorosilane at 150° C. for 10 hours [yield: 65%].

EXAMPLE 10

Reduction of (Trichloromethyl)methyldichlorosilane Using Chloroplatinic Acid i) According to the same procedure as in Example 4 i), 2.52 g of (dichloromethyl)methyldichlorosilane of which one chlorine atom of (trichloromethyl)methyldichlorosilane has been substituted with hydrogen, is obtained by reacting 3.49 g(15 mmol) of (trichloromethyl)methyldichlorosilane at 150° C. for 16 hours [yield: 85%].

ii) According to the same procedure as in Example 4 ii), 1.47 g of (chloromethyl)methyldichlorosilane of which two chlorine atoms of (trichloromethyl)methyldichlorosilane have been substituted with hydrogen, is obtained by reacting 3.49 g(15 mmol) of (trichloromethyl)methyldichlorosilane at 150° C. for 32 hours [yield: 60%].

EXAMPLE 11

Reduction of (Trichloromethyl)methyldichlorosilane Using Platinum Adsorbed on Alumina i) According to the same procedure as in Example 5 i), 2.37 g of (dichloromethyl)methyldichlorosilane of which one chlorine atom of (trichloromethyl)methyldichlorosilane has been substituted with hydrogen, is obtained by reacting 3.49 g(15 mmol) of (trichloromethyl)methyldichlorosilane at 150° C. for 9 hours [yield: 80%].

ii) According to the same procedure as in Example 5 ii), 1.52 g of (chloromethyl)methyldichlorosilane of which two chlorine atoms of (trichloromethyl)methyldichlorosilane have been substituted with hydrogen, is obtained by reacting 3.49 g(15 mmol) of (trichloromethyl)methyldichlorosilane at 150° C. for 1 hour [yield: 62%].

EXAMPLE 12

Reduction of (Trichloromethyl)methyldichlorosilane Using Platinum Adsorbed on Active Charcoal i) According to the same procedure as in Example 6 i), 2.43 g of (dichloromethyl)methyldichlorosilane of which one chlorine atom of (trichloromethyl)methyldichlorosilane has been substituted with hydrogen, is obtained by reacting 3.49 g(15 mmol) of (trichloromethyl)methyldichlorosilane at 150° C. for 28 hours [yield: 85%].

ii) According to the same procedure as in Example 6 ii), 1.47 g of (chloromethyl)methyldichlorosilane of which two chlorine atoms of (trichloromethyl)methyldichlorosilane have been substituted with hydrogen, is obtained by reacting 3.49 g(15 mmol) of (trichloromethyl)methyldichlorosilane at 150° C. for 50 hours [yield: 60%].

EXAMPLE 13

Reduction of (Dichloromethyl)trichlorosilane Using Bis(triphenylphosphine)dichloronickel i) According to the same procedure as in Example 1 i), 2.26 g of (chloromethyl)trichlorosilane of which one chlorine atom of (dichloromethyl)trichlorosilane has been substituted with hydrogen, is obtained by reacting 3.28 g(15 mmol) of (dichloromethyl)trichlorosilane at 150° C. for 30 minutes [yield: 82%, b.p. 177°–178° C.].

$^1$H NMR (ppm, CDCl$_3$) δ 3.28(s,CH$_1$)

ii) According to the same procedure as in Example 1 ii), 1.57 g of methyltrichlorosilane of which two chlorine atoms of (dichloromethyl)trichlorosilane have been substituted with hydrogen, is obtained by reacting 3.28 g(15 mmol) of (dichloromethyl)trichlorosilane at 150° C. for 1.5 hours [yield: 70%, b.p.: 65°–67° C.].

$^1$H NMR (ppm, CDCl$_3$) δ 1.13(s,3H,SiCH$_3$)

EXAMPLE 14

Reduction of (dichloromethyl)trichlorosilane using palladium diacetate i) According to the same procedure as in Example 2 i), 2.34 g of (chloromethyl)trichlorosilane of which one chlorine atom of (dichloromethyl)trichlorosilane has been substituted with hydrogen, is obtained by reacting 3.28 g(15 mmol) of (dichloromethyl)trichlorosilane at 150° C. for 45 minutes [yield: 85%].

ii) According to the same procedure as in Example 2 ii), 1.61 g of methyltrichlorosilane of which two chlorine atoms of (dichloromethyl)trichlorosilane have been substituted with hydrogen, is obtained by reacting 3.28 g(15 mmol) of (dichloromethyl)trichlorosilane at 150° C. for 2 hours [yield: 72%].

EXAMPLE 15

Reduction of (Dichloromethyl)trichlorosilane Using Dichloropalladium i) According to the same procedure as in Example 3 i), 2.21 g of (chloromethyl)trichlorosilane of which one chlorine atom of (dichloromethyl)trichlorosilane has been substituted with hydrogen, is obtained by reacting 3.28 g(15 mmol) of (dichloromethyl)trichlorosilane at 150° C. for 7 hours [yield: 80%].

ii) According to the same procedure as in Example 3 ii), 1.68 g of methyltrichlorosilane of which two chlorine atoms of (dichloromethyl)trichlorosilane have been substituted with hydrogen, is obtained by reacting 3.28 g(15 mmol) of (dichloromethyl)trichlorosilane at 150° C. for 15 hours [yield: 75%].

EXAMPLE 16

Reduction of (Dichloromethyl)trichlorosilane Using Chloroplatinic Acid i) According to the same procedure as in Example 4 i), 2.29 g of (chloromethyl)trichlorosilane of which one chlorine atom of (dichloromethyl)trichlorosilane has been substituted with hydrogen, is obtained by reacting 3.28 g(15 mmol) of (dichloromethyl)trichlorosilane at 150° C. for 16 hours [yield: 83%].

ii) According to the same procedure as in Example 4 ii), 1.34 g of methyltrichlorosilane of which two chlorine atoms of (dichloromethyl)trichlorosilane have been substituted with hydrogen, is obtained by reacting 3.28 g(15 mmol) of (dichloromethyl)trichlorosilane at 150° C. for 30 hours [yield: 60%].

EXAMPLE 17

Reduction of (Dichloromethyl)trichlorosilane Using Platinum Adsorbed on Alumina i) According to the same procedure as in Example 5 i), 1.97 g of (chloromethyl)trichlorosilane of which one chlorine atom of (dichloromethyl)trichlorosilane has been substituted with hydrogen, is obtained by reacting 3.28 g(15 mmol) of (dichloromethyl)trichlorosilane at 150° C. for 10 hours [yield: 72%].

ii) According to the same procedure as in Example 5 ii), 1.46 g of methyltrichlorosilane of which two chlorine atoms of (dichloromethyl)trichlorosilane have been substituted with hydrogen, is obtained by reacting 3.28 g(15 mmol) of (dichloromethyl)trichlorosilane at 150° C. for 25 hours [yield: 82%].

EXAMPLE 18

Reduction of (Dichloromethyl)trichlorosilane Using Platinum Adsorbed on Active Charcoal i) According to the same procedure as in Example 6 i), 1.93 g of (chloromethyl)trichlorosilane of which one chlorine atom of (dichloromethyl)trichlorosilane has been substituted with hydrogen, is obtained by reacting 3.28 g(15 mmol) of (dichloromethyl)trichlorosilane at 150° C. for 29 hours [yield: 70%].

ii) According to the same procedure as in Example 6 ii), 1.23 g of methyltrichlorosilane of which two chlorine atoms of (dichloromethyl)trichlorosilane have been substituted with hydrogen, is obtained by reacting 3.28 g(15 mmol) of (dichloromethyl)trichlorosilane at 150° C. for 50 hours [yield: 55%].

EXAMPLE 19

Reduction of (Dichloromethyl)methyldichlorosilane Using Bis(triphenylphosphine)dichloronickel i) According to the same procedure as in Example 1 i), 1.72 g of (chloromethyl)methyldichlorosilane of which one chlorine atom of (dichloromethyl)methyldichlorosilane has been substituted with hydrogen, is obtained by reacting 2.97 g(15 mmol) of (dichloromethyl)methyldichlorosilane at 150° C. for 1 hour [yield: 70%, b.p. 121°–122° C.].

$^1$H NMR (ppm, CDCl$_3$) δ 0.92(s,3H,SiCH$_3$), 3.12(s,2H, CH$_2$ )

ii) According to the same procedure as in Example 1 ii), 1.20 g of dimethyldichlorosilane of which two chlorine atoms of (dichloromethyl)methyldichlorosilane have been substituted with hydrogen, is obtained by reacting 2.97 g(15 mmol) of (dichloromethyl)methyldichlorosilane at 150° C. for 3 hours [yield: 62%, b.p.: 69°–71° C.].

$^1$H NMR (ppm, CDCl$_3$) δ 0.80(s,SiCH$_3$)

EXAMPLE 20

Reduction of (Dichloromethyl)methyldichlorosilane Using Palladium Diacetate i) According to the same procedure as in Example 2 i), 1.79 g of (chloromethyl)methyldichlorosilane of which one chlorine atom of (dichloromethyl)methyldichlorosilane has been substituted with hydrogen, is obtained by reacting 2.97 g(15 mmol) of (dichloromethyl)methyldichlorosilane at 150° C. for 1 hour [yield: 73%].

ii) According to the same procedure as in Example 2 ii), 1.37 g of dimethyldichlorosilane of which two chlorine atoms of (dichloromethyl)methyldichlorosilane have been substituted with hydrogen is obtained by reacting 2.97 g(15 mmol) of (dichloromethyl)methyldichlorosilane at 150° C. for 3 hours [yield: 71%].

EXAMPLE 21

Reduction of (Dichloromethyl)methyldichlorosilane Using Dichloropalladium i) According to the same procedure as in Example 3 i), 1.86 g of (chloromethyl)methyldichlorosilane of which one chlorine atom of (dichloromethyl)methyldichlorosilane has been substituted with hydrogen, is obtained by reacting 2.97 g(15 mmol) of (dichloromethyl)methyldichlorosilane at 150° C. for 7 hours [yield: 76%].

ii) According to the same procedure as in Example 3 ii), 1.36 g of dimethyldichlorosilane of which two chlorine atoms of (dichloromethyl)methyldichlorosilane have been substituted with hydrogen, is obtained by reacting 2.97 g(15 mmol) of (dichloromethyl)methyldichlorosilane at 150° C. for 15 hours [yield: 70%].

EXAMPLE 22

Reduction of (Dichloromethyl)methyldichlorosilane Using Chloroplatinic Acid i) According to the same procedure as in Example 4 i), 1.96 g of (chloromethyl)methyldichlorosilane of which one chlorine atom of (dichloromethyl)methyldichlorosilane has been substituted with hydrogen, is obtained by reacting 2.97 g(15 mmol) of (dichloromethyl)methyldichlorosilane at 150° C. for 18 hours [yield: 80%].

ii) According to the same procedure as in Example 4 ii), 1.16 g of dimethyldichlorosilane of which two chlorine atoms of (dichloromethyl)methyldichlorosilane have been substituted with hydrogen, is obtained by reacting 2.97 g(15 mmol) of (dichloromethyl)methyldichlorosilane at 150° C. for 40 hours [yield: 60%].

EXAMPLE 23

Reduction of (Dichloromethyl)methyldichlorosilane Using Platinum Adsorbed on Alumina i) According to the same procedure as in Example 5 i), 2.08 g of (chloromethyl)methyldichlorosilane of which one chlorine atom of (dichloromethyl)methyldichlorosilane has been substituted with hydrogen, is obtained by reacting 2.97 g(15 mmol) of (dichloromethyl)methyldichlorosilane at 150° C. for 11 hour [yield: 85%].

ii) According to the same procedure as in Example 5 ii), 1.22 g of dimethyldichlorosilane of which two chlorine atoms of (dichloromethyl)methyldichlorosilane have been substituted with hydrogen, is obtained by reacting 2.97 g(15 mmol) of (dichloromethyl)methyldichlorosilane at 150° C. for 20 hours [yield: 63%].

EXAMPLE 24

Reduction of (Dichloromethyl)methyldichlorosilane Using Platinum Adsorbed on Active Charcoal i) According to the same procedure as in Example 6 i), 1.96 g of (chloromethyl)methyldichlorosilane of which one chlorine atom of (dichloromethyl)methyldichlorosilane has been substituted with hydrogen, is obtained by reacting 2.97 g(15 mmol) of (dichloromethyl)methyldichlorosilane at 150° C. for 30 hours [yield: 80%].

ii) According to the same procedure as in Example 6 ii), 0.95 g of dimethyldichlorosilane of which two chlorine atoms of (dichloromethyl)methyldichlorosilane have been substituted with hydrogen, is obtained by reacting 2.97 g(15 mmol) of (dichloromethyl)methyldichlorosilane at 150° C. for 48 hours [yield: 50%].

EXAMPLE 25

Reduction of (Dichloromethyl)dimethylchlorosilane Using Bis(triphenylphosphine)dichloronickel i) According to the same procedure as in Example 1 i), 1.76 g of (chloromethyl)dimethylchlorosilane of which one chlorine atom of (dichloromethyl)dimethylchlorosilane has been substituted with hydrogen, is obtained by reacting 2.97 g(15 mmol) of (dichloromethyl)dimethylchlorosilane at 150° C. for 1 hour [yield: 83%, b.p. 115°–116° C.].

$^1$H NMR (ppm, CDCl$_3$) δ 0.52(s,6H,SiCH$_3$), 2.95(s,2H, CH$_2$)

ii) According to the same procedure as in Example 1 ii), 1.29 g (calculated value from area ratio from gas chromatography equipped with thermal conductivity analyzer) of trimethylchlorosilane of which two chlorine atoms of (dichloromethyl)dimethylchlorosilane have been substituted with hydrogen, is obtained by reacting 2.97 g(15 mmol) of (dichloromethyl)dimethylchlorosilane at 150° C. for 3 hours [yield: 79%, b.p.: 56°–58° C.].

$^1$H NMR (ppm, CDCl$_3$) δ 0.43(s,SiCH$_3$)

EXAMPLE 26

Reduction of (Dichloromethyl)dimethylchlorosilane Using Palladium Diacetate i) According to the same procedure as in Example 2 i), 1.69 g of (chloromethyl)dimethylchlorosilane of which one chlorine atom of (dichloromethyl)dimethylchlorosilane has been substituted with hydrogen, is obtained by reacting 2.97 g(15 mmol) of (dichloromethyl)dimethylchlorosilane at 150° C. for 1.5 hours [yield: 80%].

ii) According to the same procedure as in Example 2 ii), 1.25 g (calculated value from area ratio from gas chromatography equipped with thermal conductivity analyzer) of trimethylchlorosilane of which two chlorine atoms of (dichloromethyl)dimethylchlorosilane have been substituted with hydrogen, is obtained by reacting 2.97 g(15 mmol) of (dichloromethyl)dimethylchlorosilane at 150° C. for 3 hours [yield: 79%].

EXAMPLE 27

Reduction of (Dichloromethyl)dimethylchlorosilane Using Dichloropalladium i) According to the same procedure as in Example 3 i), 1.69 g of (chloromethyl)dimethylchlorosilane of which one chlorine atom of (dichloromethyl)dimethylchlorosilane has been substituted with hydrogen, is obtained by reacting 2.97 g(15 mmol) of (dichloromethyl)dimethylchlorosilane at 150° C. for 7.5 hours [yield: 80%].

ii) According to the same procedure as in Example 3 ii), 1.24 g (calculated value from area ratio from gas chromatography equipped with thermal conductivity analyzer) of trimethylchlorosilane of which two chlorine atoms of (dichloromethyl)dimethylchlorosilane have been substituted with hydrogen, is obtained by reacting 2.97 g(15 mmol) of (dichloromethyl)dimethylchlorosilane at 150° C. for 15 hours [yield: 76%].

EXAMPLE 28

Reduction of (Dichloromethyl)dimethylchlorosilane Using Chloroplatinic Acid i) According to the same procedure as in Example 4 i), 1.61 g of (chloromethyl)dimethylchlorosilane of which one chlorine atom of (dichloromethyl)dimethylchlorosilane has been substituted with hydrogen, is obtained by reacting 2.97 g(15 mmol) of (dichloromethyl)dimethylchlorosilane at 150° C. for 20 hours [yield: 76%].

ii) According to the same procedure as in Example 4 ii), 1.14 g (calculated value from area ratio from gas chromatography equipped with thermal conductivity analyzer) of trimethylchlorosilane of which two chlorine atoms of (dichloromethyl)dimethylchlorosilane have been substituted with hydrogen, is obtained by reacting 2.97 g(15 mmol) of (dichloromethyl)dimethylchlorosilane at 150° C. for 45 hours [yield: 70%].

EXAMPLE 29

Reduction of (Dichloromethyl)dimethylchlorosilane Using Platinum Adsorbed on Alumina i) According to the same procedure as in Example 5 i), 1.52 g of (chloromethyl)dimethylchlorosilane of which one chlorine atom of (dichloromethyl)dimethylchlorosilane has been substituted with hydrogen, is obtained by reacting 2.97 g(15 mmol) of (dichloromethyl)dimethylchlorosilane at 150° C. for 11 hours [yield: 72%].

ii) According to the same procedure as in Example 5 ii), 1.01 g (calculated value from area ratio from gas chromatography equipped with thermal conductivity analyzer) of trimethylchlorosilane of which two chlorine atoms of (dichloromethyl)dimethylchlorosilane have been substituted with hydrogen, is obtained by reacting 2.97 g(15 mmol) of (dichloromethyl)dimethylchlorosilane at 150° C. for 20 hours [yield: 68%].

EXAMPLE 30

Reduction of (Dichloromethyl)dimethylchlorosilane Using Platinum Adsorbed on Active Charcoal i) According to the same procedure as in Example 6 i), 1.48 g of (chloromethyl)dimethylchlorosilane of which one chlorine atom of (dichloromethyl)dimethylchlorosilane has been substituted with hydrogen, is obtained by reacting 2.97 g(15 mmol) of (dichloromethyl)dimethylchlorosilane at 150° C. for 34 hours [yield: 70%].

ii) According to the same procedure as in Example 6 ii), 1.06 g (calculated value from area ratio from gas chromatography equipped with thermal conductivity analyzer) of trimethylchlorosilane of which two chlorine atoms of (dichloromethyl)dimethylchlorosilane have been substituted with hydrogen, is obtained by reacting 2.97 g(15 mmol) of (dichloromethyl)dimethylchlorosilane at 150° C. for 48 hours [yield: 65%].

EXAMPLE 31

Reduction of (Dichloromethyl)trimethylsilane Using Bis(triphenylphosphine)dichloronickel i) According to the same procedure as in Example 1 i), 1.47 g of (chloromethyl)trimethylsilane of which one chlorine atom of (dichloromethyl)trimethylsilane has been substituted with hydrogen, is obtained by reacting 2.66 g(15 mmol) of (dichloromethyl)trimethylsilane at 150° C. for 1.5 hours [yield: 80%, b.p. 97°–98° C.].

$^1$H NMR (ppm, CDCl$_3$) δ 0.12(s,9H,SiCH$_3$), 2.77(s,2H, CH$_2$)

ii) According to the same procedure as in Example 1 ii), 0.69 g (calculated value from area ratio from gas chromatography equipped with thermal conductivity analyzer) of tetramethylsilane of which two chlorine atoms of (dichloromethyl)trimethylsilane have been substituted with hydrogen is obtained by reacting 2.66 g(15 mmol) of (dichloromethyl)trimethylsilane at 150° C. for 3 hours [yield: 52%, b.p.: 25°–27° C.].

$^1$H NMR (ppm, CDCl$_3$) δ 0.00(s,SiCH$_3$)

EXAMPLE 32

Reduction of (Dichloromethyl)trimethylsilane Using Palladium Diacetate i) According to the same procedure as in Example 2 i), 1.54 g of (chloromethyl)trimethylsilane of which one chlorine atom of (dichloromethyl)trimethylsilane has been substituted with hydrogen is obtained by reacting 2.66 g(15 mmol) of (dichloromethyl)trimethylsilane at 150° C. for 2 hours [yield: 85%].

ii) According to the same procedure as in Example 2 ii), 0.82 g (calculated value from area ratio from gas chromatography equipped with thermal conductivity analyzer) of tetramethylsilane of which two chlorine atoms of (dichloromethyl)trimethylsilane have been substituted with hydrogen is obtained by reacting 2.66 g(15 mmol) of (dichloromethyl)trimethylsilane at 150° C. for 5 hours [yield: 62%].

EXAMPLE 33

Reduction of (Dichloromethyl)trimethylsilane Using Dichloropalladium i) According to the same procedure as in Example 3 i), 1.36 g of (chloromethyl)trimethylsilane of which one chlorine atom of (dichloromethyl)trimethylsilane has been substituted with hydrogen is obtained by reacting 2.66 g(15 mmol) of (dichloromethyl)trimethylsilane at 150° C. for 8 hours [yield: 75%].

ii) According to the same procedure as in Example 3 ii), 0.81 g (calculated value from area ratio from gas chromatography equipped with thermal conductivity analyzer) of tetramethylsilane of which two chlorine atoms of (dichloromethyl)trimethylsilane have been substituted with hydrogen is obtained by reacting 2.66 g(15 mmol) of (dichloromethyl)trimethylsilane at 150° C. for 20 hours [yield: 61%].

EXAMPLE 34

Reduction of (Dichloromethyl)trimethylsilane Using Chloroplatinic Acid i) According to the same procedure as in Example 4 i), 1.36 g of (chloromethyl)trimethylsilane of which one chlorine atom of (dichloromethyl)trimethylsilane has been substituted with hydrogen, is obtained by reacting 2.66 g(15 mmol) of (dichloromethyl)trimethylsilane at 150° C. for 24 hours [yield: 75%].

ii) According to the same procedure as in Example 4 ii), 0.82 g (calculated value from area ratio from gas chromatography equipped with thermal conductivity analyzer) of tetramethylsilane of which two chlorine atoms of (dichloromethyl)trimethylsilane have been substituted with hydrogen, is obtained by reacting 2.66 g(15 mmol) of (dichloromethyl)trimethylsilane at 150° C. for 48 hours [yield: 62%].

EXAMPLE 35

Reduction of (Dichloromethyl)trimethylsilane Using Platinum Adsorbed on Alumina i) According to the same procedure as in Example 5 i), 1.45 g of (chloromethyl)trimethylsilane of which one chlorine atom of (dichloromethyl)trimethylsilane has been substituted with hydrogen, is obtained by reacting 2.66 g(15 mmol) of (dichloromethyl)trimethylsilane at 150° C. for 12 hours [yield: 80%].

ii) According to the same procedure as in Example 5 ii), 0.55 g (calculated value from area ratio from gas chromatography equipped with thermal conductivity analyzer) of tetramethylsilane of which two chlorine atoms of (dichloromethyl)trimethylsilane have been substituted with hydrogen, is obtained by reacting 2.66 g(15 mmol) of (dichloromethyl)trimethylsilane at 150° C. for 24 hours [yield: 42%].

EXAMPLE 36

Reduction of (Dichloromethyl)trimethylsilane Using Platinum Adsorbed on Active Charcoal i) According to the same procedure as in Example 6 i), 1.50 g of (chloromethyl)trimethylsilane of which one chlorine atom of (dichloromethyl)trimethylsilane has been substituted with hydrogen, is obtained by reacting 2.66 g(15 mmol) of (dichloromethyl)trimethylsilane at 150° C. for 35 hours [yield: 83%].

ii) According to the same procedure as in Example 6 ii), 0.83 g (calculated value from area ratio from gas chromatography equipped with thermal conductivity analyzer) of tetramethylsilane of which two chlorine atoms of (dichloromethyl)trimethylsilane have been substituted with hydrogen is obtained by reacting 2.66 g(15 mmol) of (dichloromethyl)trimethylsilane at 150° C. for 1 hour [yield: 62%].

What is claimed is:

1. A process for preparation of silane compound represented by general formula (I) of which one or two hydrogens have been substituted, comprising a reaction of silane compound represented by general formula (II) with trichlorosilane in the presence of metal or metal compound as a catalyst.

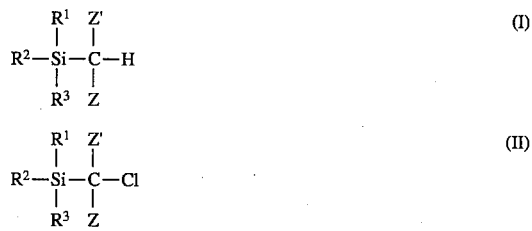

whereby, $R^1$, $R^2$ and $R^3$ respectively represent chlorine or methyl group, and Z and Z' respectively represent hydrogen or chlorine.

2. A process according to claim 1, wherein the catalyst of metal or metal compound is selected from a group consisting of bis(triphenylphosphine)dichloronickel, palladium diacetate, dichloropalladium, chloroplatinic acid, platinum adsorbed on alumina, platinum adsorbed on active charcoal.

3. A process according to claim 1, wherein the amount of trichlorosilane used is 2–40 folds by mole of the compound of general formula (II).

4. A process according to claim 1, wherein the amount of catalyst used is 0.01–20% by mole of the compound of general formula (II).

5. A process according to claim 1, wherein the reaction temperature is 50°–200° C.

6. A process according to claim 2, wherein the amount of catalyst used is 0.01–20% by mole of the compound of general formula (II).

* * * * *